United States Patent
Tilly et al.

(10) Patent No.: US 10,525,086 B2
(45) Date of Patent: Jan. 7, 2020

(54) METHODS FOR GROWTH AND MATURATION OF OVARIAN FOLLICLES

(71) Applicant: NORTHEASTERN UNIVERSITY, Boston, MA (US)

(72) Inventors: Jonathan L. Tilly, Windham, NH (US); Dori C. Woods, Londonderry, NH (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 15/126,680

(22) PCT Filed: Mar. 27, 2014

(86) PCT No.: PCT/US2014/032010
§ 371 (c)(1),
(2) Date: Sep. 16, 2016

(87) PCT Pub. No.: WO2015/147830
PCT Pub. Date: Oct. 1, 2015

(65) Prior Publication Data
US 2017/0087192 A1 Mar. 30, 2017
US 2018/0289748 A9 Oct. 11, 2018

Related U.S. Application Data

(60) Provisional application No. 61/887,569, filed on Oct. 7, 2013.

(51) Int. Cl.
| | |
|---|---|
| *A61K 35/54* | (2015.01) |
| *A61K 35/545* | (2015.01) |
| *C12N 5/075* | (2010.01) |
| *C12N 15/11* | (2006.01) |
| *C12N 15/113* | (2010.01) |
| *C12N 15/63* | (2006.01) |
| *A61K 35/12* | (2015.01) |
| *C12N 5/073* | (2010.01) |

(52) U.S. Cl.
CPC .............. *A61K 35/54* (2013.01); *A61K 35/12* (2013.01); *C12N 5/0605* (2013.01); *C12N 5/0609* (2013.01); *C12N 2502/025* (2013.01); *C12N 2506/02* (2013.01); *C12N 2510/00* (2013.01); *C12N 2740/16043* (2013.01)

(58) Field of Classification Search
CPC ... A61K 35/54; C12N 2506/02; C12N 5/0609
See application file for complete search history.

(56) References Cited

U.S. PATENT DOCUMENTS

| | | |
|---|---|---|
| 2006/0010508 A1 | 1/2006 | Tilly et al. |
| 2012/0087898 A1 | 4/2012 | Tilly et al. |
| 2012/0195861 A1 | 8/2012 | Tilly et al. |

FOREIGN PATENT DOCUMENTS

| | | |
|---|---|---|
| EP | 0723453 B1 | 3/2000 |
| WO | WO-2007/009166 A1 | 1/2007 |
| WO | WO-2015/054315 A1 | 4/2015 |

OTHER PUBLICATIONS

Lana et al 2012, Advanced Drug Delivery Rev. 64:200-216.*
Nakamura et al 2008, Molecular Reproduction and Development 75:472-476.*
Lan et al 2013, J. Clin. Endocrinol. Metab. 98:3713-3723.*
Woods et al 2012, Fertil. Steril. 98:3-10.*
Liu et al 2013 Jan, Genetics and Molecular Research 12:127-135.*
Combelles et al, In vitro maturation of human oocytes and cumulus cells using a co-culture three-dimensional collagen gel system, Human Reproduction vol. 20, No. 5 pp. 1349-1358, 2005.*
Benayoun et al, The identification and characterization of a FOXL2 response element provides insights into the pathogenesis of mutant alleles, Human Molecular Genetics, 2008, vol. 17, No. 20 3118-3127.*
Woods, C. et al., Embryonic Stem Cell-Derived Granulosa Cells Participate in Ovarian Follicle Formation In Vitro and In Vivo, Mar. 27, 2013, vol. 20, No. 5; pp. 524-535; abstract p. 525.
Hsu et al., "Gonadotropins and estradiol stimulate immunoreactive insulin-like growth factor-I production by porcine granulosa cells in vitro," *Endocrinology*, 120(1):198-207 (Abstract)(1987).
Hu et al., "GSK3 Inhibitor-BIO regulates proliferation of female germline stem cells from the postnatal mouse ovary," *Cell Proliferation*, 45(4):287-298 (2012).
Woods et al., "Isolation, characterization and propagation of mitotically active germ cells from adult mouse and human ovaries," *Nature Protocols*, 8(5):966-988 (2013).

\* cited by examiner

*Primary Examiner* — Maria Marvich
(74) *Attorney, Agent, or Firm* — Foley Hoag LLP

(57) ABSTRACT

The present technology provides for methods for generation and isolation of granulosa cells and/or granulosa cell precursors from multi-potent cells, wherein the granulosa cells and/or granulosa cell precursors are useful in methods for growth and maturation of follicles or follicle-like structures. Additionally, the present technology also provides for methods of increasing steroidal hormones in a subject in need thereof.

6 Claims, 8 Drawing Sheets

A

B

H: Chr 3: 140147124 – 140149524
M: Chr 9: 98857207 – 98859607

C  Granulosa cells

Brightfield     *Foxl2*-DsRed 293 cells

Brightfield     *Foxl2*-DsRed

METHODS FOR GROWTH AND MATURATION OF OVARIAN FOLLICLES

GOVERNMENT SUPPORT

The present technology was made with U.S. Government support under grant R37-AG012279 and F32-AG034809 awarded by the National Institutes of Health. The U.S. Government has certain rights in the present technology.

RELATED APPLICATIONS

This application is a § 371 national-stage application based on Patent Cooperation Treaty Application serial number PCT/US2014/032010, filed Mar. 27, 2014.

BACKGROUND

Follicle-like structures formed by mouse embryonic stem cells (ESCs) in vitro consist of a single oocyte-like cell, which can grow as large as 70 μm in diameter, surrounded by one or more layers of tightly-adherent somatic cells. Analogous to what is observed during normal follicle formation within the ovary, somatic cells within ESC-derived follicle-like structures are connected via intercellular bridges with their enclosed germ cells, which may serve to facilitate cell-to-cell interaction required for normal follicle development.

SUMMARY

In one aspect, the present technology provides a method to promote the growth and maturation of a mammalian oocyte in a subject. The method includes: engineering mammalian multi-potent cells to contain a granulosa cell specific reporter, wherein expression of the granulosa cell specific reporter is indicative of a cell that is a granulosa cell or a granulosa cell precursor, culturing the mammalian multi-potent cells in vitro, under conditions suitable for differentiation of the multi-potent cells to granulosa cells or granulosa cell precursors, isolating an enriched population of granulosa cells or granulosa cell precursors based on expression of the granulosa cell specific reporter, and contacting the enriched population of granulosa cells or granulosa cell precursors with mammalian ovarian tissue, wherein the mammalian ovarian tissue comprises a follicle and/or an immature oocyte, wherein the granulosa cells or granulosa cell precursors promote the growth and maturation of the follicle and/or the immature oocyte.

In some embodiments, the population of granulosa cells or granulosa cell precursors and the mammalian ovarian tissue are autologous.

In some embodiments, the mammalian ovarian tissue is human.

In some embodiments, the granulosa cell specific reporter comprises a fluorescent reporter under control of an ovarian granulosa cell-specific gene.

In some embodiments, the ovarian granulosa cell-specific gene is selected from the group consisting of: forkhead box L2 (Foxl2), wingless type MMTV integration site family, member 4 (WNT4), Nr5a1, Dax-1, ATP-binding cassette, subfamily 9 (Abca9), acetyl-Coenzyme A acyltransferase 2 (mitochondrial 3-oxoacyl-Coenzyme A thiolase; Acaa2), actin, alpha 2, smooth muscle, aorta (Acta2), a disintegrin-like and metallopeptidase (reprolysin-like) with thrombosin type 1 motif, 17 (Adamts17), ADAMTS-like 2 (Adamts12), AF4/FMR2 family, member 1 (Aff1), expressed sequence AI314831 (AI314831), Aldo-keto reductase family 1, member C14 (Akr1c14), aldo-keto reductase family 1, Notch2, and member C-like (Akr1c1).

In some embodiments, the fluorescent reporter is selected from the group consisting of: DsRed, green fluorescent protein (GFP), yellow fluorescent protein (YFP), and orange fluorescent protein (OFP).

In some embodiments, contacting the enriched population of granulosa cells or granulosa cell precursors with mammalian ovarian tissue is performed ex vivo. In some embodiments, contacting the enriched population of granulosa cells or granulosa cell precursors with mammalian ovarian tissue is performed in vivo.

In some embodiments, the mammalian multi-potent cells are selected from the group consisting of: embryonic stem cells (ESCs), induce pluripotent stem cells (iPSCs), bone marrow derived cells, and peripheral blood-derived cells.

In another aspect, the present technology provides methods for increasing levels of one or more steroidal hormones in a subject in need thereof. The method including, engineering a plurality of mammalian multi-potent cells to contain a granulosa cell specific reporter, wherein expression of the granulosa cell specific reporter is indicative of a cell that is a granulosa cell or a granulosa cell precursor, culturing the plurality of mammalian multi-potent cells in vitro, under conditions suitable for differentiation of the mammalian multi-potent cells to granulosa cells or granulosa cell precursors, isolating an enriched population of granulosa cells or granulosa cell precursors based on expression of the granulosa cell specific reporter, and administering an effective amount of the enriched population of granulosa cells or granulosa cell precursors to the subject, wherein the granulosa cells or granulosa cell precursors secrete one or more steroidal hormones, and wherein after administration of the enriched population of granulosa cells or granulosa cell precursors the subject displays elevated levels of one or more steroidal hormone as compared to the subject before administration of the enriched population of granulosa cells or granulosa cell precursors.

In some embodiments, the method also includes stimulating the granulosa cells or granulosa cell precursors to secrete steroidal hormones.

In some embodiments, the steroidal hormones selected from the group consisting of: estradiol, estriol, estrone, pregnenolone, and progesterone.

In some embodiments, the granulosa cells or granulosa cell precursors are stimulated to secrete steroidal hormones by follicle-stimulating hormone (FSH), 8-Bromoadenosine 3',5'-cyclic monophosphate (8-br-cAMP), and luteinizing hormone (LH).

In some embodiments, the population of granulosa cells or granulosa cell precursors autologous to the subject.

In some embodiments, the subject is human.

In some embodiments, the granulosa cell specific reporter comprises a fluorescent reporter under control of an ovarian granulosa cell-specific gene.

In some embodiments, the ovarian granulosa cell-specific gene is selected from the group consisting of: forkhead box L2 (Foxl2), wingless type MMTV integration site family, member 4 (WNT4), Nr5a1, Dax-1, ATP-binding cassette, subfamily 9 (Abca9), acetyl-Coenzyme A acyltransferase 2 (mitochondrial 3-oxoacyl-Coenzyme A thiolase; Acaa2), actin, alpha 2, smooth muscle, aorta (Acta2), a disintegrin-like and metallopeptidase (reprolysin-like) with thrombosin type 1 motif, 17 (Adamts17), ADAMTS-like 2 (Adamts12), AF4/FMR2 family, member 1 (Aff1), expressed sequence AI314831 (AI314831), Aldo-keto reductase family 1, member C14 (Akr1c14), aldo-keto reductase family 1, Notch2, and member C-like (Akr1c1).

In some embodiments, the fluorescent reporter is selected from the group consisting of: DsRed, green fluorescent protein (GFP), yellow fluorescent protein (YFP), and orange fluorescent protein (OFP).

In some embodiments, the granulosa cells or granulosa cell precursors are stimulated before administration. In some embodiments, the granulosa cells or granulosa cell precursors are stimulated after administration.

In some embodiments, the mammalian multi-potent cells are selected from the group consisting of: embryonic stem cells (ESCs), induced pluripotent stem cells (iPSCs) or otherwise reprogrammed somatic cells, bone marrow derived cells, and peripheral blood-derived cells.

In some embodiments, the subject suffers from a reduced or lack of secretion of steroidal hormones. In some embodiments, the reduced or lack of secretion of steroidal hormones is due to a condition selected from the group consisting of menopause, ovariectomy, hysterectomy, premature ovarian failure, primary ovarian insufficiency, chemotherapy-induced ovarian failure, Turner's syndrome.

DETAILED DESCRIPTION

Figure 1:
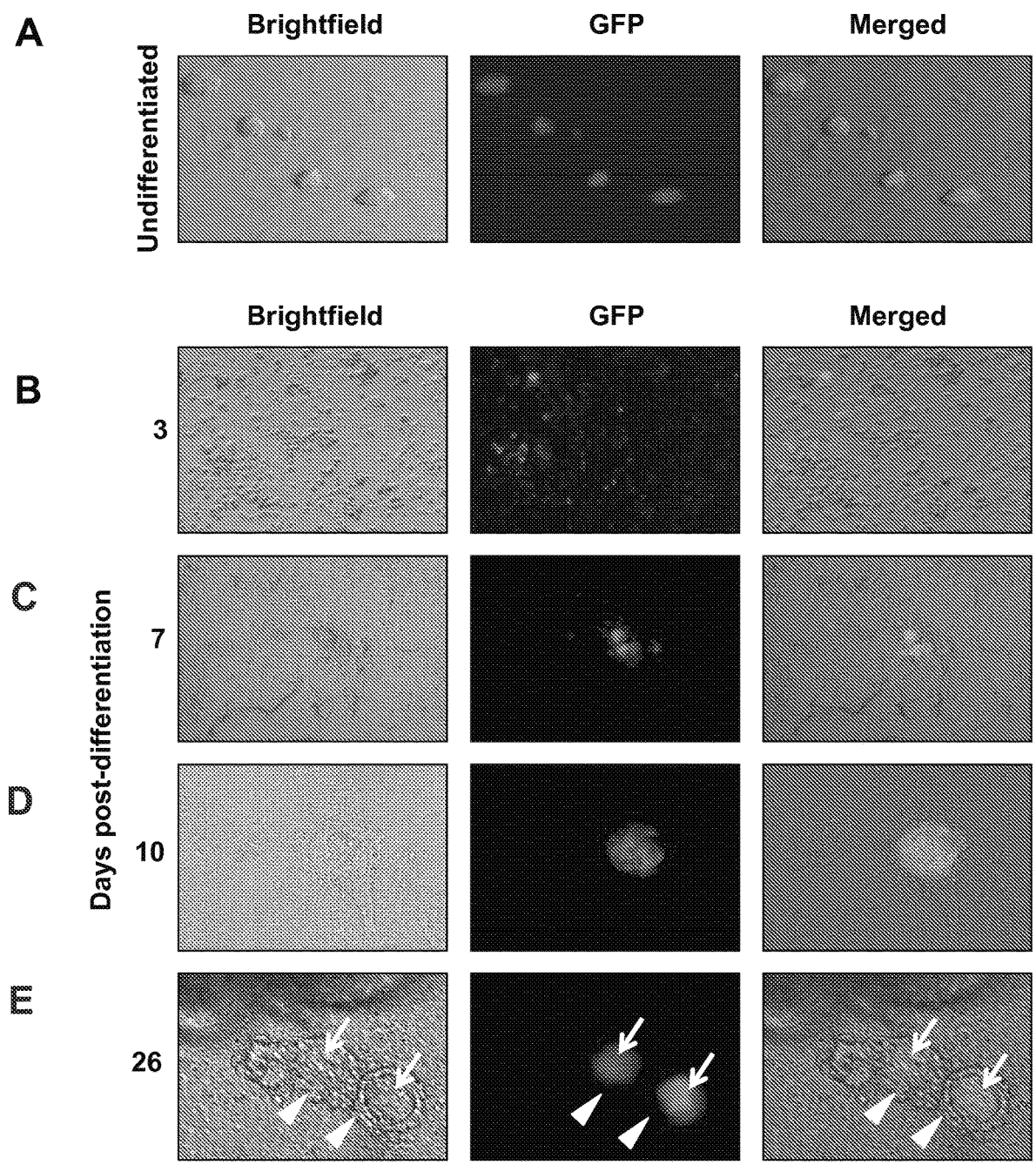
FIG. 1A is an image showing undifferentiated mouse TgOG2 ESC line with germ cell lineage expression of green fluorescent protein (GFP).
FIG. 1B is an image showing TgOG2 ESC line with germ cell lineage expression of GFP 3 days post-differentiation.
FIG. 1C is an image showing TgOG2 ESC line with germ cell lineage expression of GFP 7 days post-differentiation.
FIG. 1D is an image showing TgOG2 ESC line with germ cell lineage expression of GFP 10 days post-differentiation.
FIG. 1E is an image showing TgOG2 ESC line with germ cell lineage expression of GFP 26 days post-differentiation.

The various concepts introduced above and discussed in greater detail below may be implemented in any of numerous ways, as the described concepts are not limited to any particular manner of implementation. Examples of specific implementations and applications are provided primarily for illustrative purposes.

As used herein, the singular forms "a," "an" and "the" include plural referents unless the content clearly dictates otherwise. For example, reference to "a cell" includes a combination of two or more cells, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, the "administration" of an agent, drug, compound, or cells to a subject includes any route of introducing or delivering to a subject an agent, drug, compound, or cells to perform its intended function. Administration can be carried out by any suitable route, including, e.g., localized injection (e.g., catheter administration or direct intra-ovarian injection), systemic injection, intravenous injection, intrauterine injection, orally, intranasally, and parenteral administration. Administration includes self-administration and the administration by another.

As used herein, "differentiation" refers to the developmental process of lineage commitment. A "lineage" refers to a pathway of cellular development, in which precursor or "progenitor" cells undergo progressive physiological changes to become a specified cell type having a characteristic function (e.g., nerve cell, muscle cell or granulosa cell). Differentiation occurs in stages, whereby cells gradually become more specified until they reach full maturity, which is also referred to as "terminal differentiation." A "terminally differentiated cell" is a cell that has committed to a specific lineage, and has reached the end stage of differentiation (i.e., a cell that has fully matured). Oocytes are an example of a terminally differentiated cell type.

As used herein, the term "enriched population" refers to a purified or semi-purified population of granulosa cells or granulosa cell precursors. In some embodiments, a specific population of granulosa cells or granulosa cell precursors is enriched by sorting the granulosa cells or granulosa cell precursors from the population of differentiating multi-potent cells, e.g., by fluorescence activated cell sorting (FACS), magnetic assisted cell sorting (MACS), or other cell purification strategies known in the art for separation of a specific populations of cells from a general population of cells. By way of example, but not by limitation, in some embodiments, an enriched population of granulosa cells or granulosa cell precursors is a purified or semi-purified population of granulosa cells or granulosa cell precursors that have been isolated from differentiating multi-potent cells by FACS.

As used herein, the term "effective amount" or "therapeutically effective amount" refers to a quantity sufficient to achieve a desired effect, e.g., an amount of granulosa cells that will elevated steroidal hormone levels in a subject in need thereof. By way of example, but not by limitation, in some embodiments, a therapeutically effective amount of granulosa cells is the amount of granulosa cells necessary to raise a subject's steroidal level as compared to a normal subject's steroidal hormone level. In the context of hormone therapy applications, in some embodiments, the amount of granulosa cells or granulosa cell precursors administered to the subject will depend on the condition or disease state of the subject, e.g., a menopause subject or subject who has had a hysterectomy, and on the characteristics of the subject, such as general health, age, sex, body weight and tolerance to drugs. The skilled artisan will be able to determine appropriate dosages depending on these and other factors.

As used herein, a "follicle" refers to an ovarian structure consisting of a single oocyte surrounded by somatic (granulosa without or with theca-interstitial) cells. Somatic cells of the gonad enclose individual oocytes to form follicles. Each fully formed follicle is enveloped in a complete basement membrane. Although some of these newly formed follicles start to grow almost immediately, most of them remain in the resting stage until they either degenerate or some signal(s) activate(s) them to enter the growth phase.

As used herein, the term "immature oocyte" refers to primary oocytes that are arrested in prophase I.

As used herein, the term "mature follicle" refers to a follicle that has actively proliferating granulosa cells surrounding a developing oocyte that responds to exogenous hormones. By way of example, but not by limitation, mature or maturing follicles increase in size due to proliferation of the granulosa cells, expansion of the oocyte following resumption of meiosis, and because of the development of a fluid filled antrum.

As used herein, the term "mature oocyte" refers to an oocyte arrested in metaphase II of meiosis capable of fertilization following sperm penetration or activation of parthenogenesis by addition of calcium ionophore.

As used herein, the term "stimulating agent" refers to any compound, hormone, peptide, drug, or other agent that stimulates granulosa cells or granulosa cell precursors to secreted steroidal hormones, e.g., estradiol or progesterone. By way for example, but not by limitation, in some embodiments, stimulating agents include but are not limited to follicle stimulating hormone (FSH) and 8-Bromoadenosine 3',5'-cyclic monophosphate (8-br-cAMP).

GENERAL BACKGROUND

Fully functional eggs have been generated from oocytes initially derived from mouse ESCs or induced pluripotent stem cells (iPSCs). Hayashi et al., *Science,* 338: 971-975 (2012). Specification of primordial germ cell (PGC)-like cells (PGCLCs) from differentiating mouse ESCs or iPSCs follows a precise time frame in vitro. PGCLCs formed between 3 to 6 days into the differentiation of ESCs or iPSCs closely resembling endogenous PGCs present in embryonic day 12.5 (e12.5) mouse ovaries. In one study, in vitro-derived PGCLCs specified 3, 4, and 6 days after initiation of ESC differentiation with dispersed e12.5 ovarian tissue were transplanted, as aggregates, under the ovarian bursal sacs of adult female mice. Hayashi et al., *Science,* 338: 971-975 (2012). The PGCLCs subsequently developed into germinal vesicle stage oocytes. Following harvesting and in vitro maturation, the oocytes underwent in vitro fertilization. After embryogenesis, the embryos were transplanted into recipient females and they developed into viable offspring. Other studies have succeeded in using female germline or oogonial stem cells purified from adult ovaries to generate fertilization competent eggs. Zou et al., *Nat Cell Biol.,* 11:631-636 (2009), Zhang et al., *J Mol Cell Biol.,* 3:132-141 (2011), and White et al., *Nat Med.,* 18:413-421 (2012).

These studies demonstrate that mouse ESCs and iPSCs can actually be differentiated, albeit at low frequency, into oocytes capable of fertilization and embryogenesis. These studies also demonstrate that PGCLCs, which resemble endogenous PGCs in fetal gonads, require interaction with developmentally matched embryonic ovary somatic cells to realize their full potential in vivo. In order to provide the micro-environmental cues necessary for oogenesis, folliculogenesis, and ultimately egg formation from PGCLCs, a source of developmentally matched ovarian somatic cells is required.

Follicle-like structures formed by mouse ESCs in vitro consist of a single oocyte-like cell, which can grow as large as 70 μm diameter, surrounded by one or more layers of tightly-adherent somatic cells. Analogous to what is observed during normal follicle formation within the ovary, somatic cells within ESC-derived follicle-like structures are connected via intercellular bridges with their enclosed germ cells, which may serve to facilitate cell-to-cell interaction required for normal follicle development. Additionally, increased expression of steroidogenic pathway genes, along with estrogen secretion into the culture medium, occurs concomitant with the formation of follicle-like structures from ESCs in vitro. While these observations collectively support the notion that somatic cells of in vitro-derived follicle-like structures have features ultra-structurally and functionally similar to endogenous granulosa cells, isolation and characterization of these cells from differentiating ESCs has been difficult.

In general the present technology relates to methods for promoting formation and growth of ovarian follicles and/or promoting oocytes maturation using enriched isolated granulosa cells derived from multi-potent cells. Additionally, the present technology also relates to methods for increasing levels of steroidal hormones in a subject by administration of enriched isolated granulosa cells derived from multi-potent cells.

Methods for Isolating Granulosa Cells or Granulosa Cell Precursors from Multi-Potent Cells In some embodiments, the present technology relates to identifying and isolating granulosa cells or granulosa cell precursors from multi-potent cells.

In some embodiments, multi-potent cells are engineered to contain at least one granulosa cell specific gene reporter, wherein expression of the granulosa cell specific gene reporter is indicative of a cell that is a granulosa cell or a granulosa cell precursor.

Multi-potent cells include, but are not limited to, embryonic stem cells (ESCs), pluripotent stem cells, induced pluripotent stem cells (iPSCs) or otherwise reprogrammed somatic cells, bone marrow derived cells, peripheral blood-derived cells.

The multi-potent cells may be any mammalian multi-potent cell. Mammals from which the multi-potent cell can originate, include, for example, farm animals, such as sheep, pigs, cows, and horses; pet animals, such as dogs and cats; laboratory animals, such as rats, mice, monkeys, and rabbits. In some embodiments, the mammal is a human.

In some embodiments, the granulosa cell specific reporter includes a fluorescent reporter under regulatory control of an ovarian granulosa cell-specific gene. Ovarian granulosa cell-specific genes include, but are not limited to, forkhead box L2 (Foxl2), wingless type MMTV integration site family, member 4 (WNT4), Nr5a1, Dax-1, ATP-binding cassette, subfamily 9 (Abca9), acetyl-Coenzyme A acyltransferase 2 (mitochondrial 3-oxoacyl-Coenzyme A thiolase; Acaa2), actin, alpha 2, smooth muscle, aorta (Acta2), a disintegrin-like and metallopeptidase (reprolysin-like) with thrombosin type 1 motif, 17 (Adamts17), ADAMTS-like 2 (Adamts12), AF4/FMR2 family, member 1 (Aff1), expressed sequence AI314831 (AI314831), Aldo-keto reductase family 1, member C14 (Akr1c14), aldo-keto reductase family 1, Notch2, and member C-like (Akr1c1). Fluorescent reporters include but are not limited to, *Discosoma* sp. red (DsRed), green fluorescent protein (GFP), yellow fluorescent protein (YFP), and orange fluorescent protein (OFP).

In some embodiments, the granulosa cell specific reporter is a non-fluorescent reporter under regulatory control of an ovarian granulosa cell-specific gene. Non-fluorescent reporters include, but are not limited to, luciferase and beta-galactosidase.

The granulosa cell specific reporter can be engineered by any methods known in the art. By way of example, but not by limitation, in some embodiments, a granulosa cell specific reporter is engineered by identifying a granulosa cell specific gene promoter, determining a conserved region of the gene promoter, isolating the conserved region from genomic DNA using PCR, and cloning the conserved region into a vector containing a fluorescent marker.

Engineering multi-potent cells to contain the granulosa cell specific gene reporter can be accomplished by any method known in the art. By way of example, but not by limitation, in some embodiments, the granulosa cell specific gene reporter is inserted into the multi-potent cells by using electroporation. Other methods for inserting the granulosa cell specific gene reporter include, but are not limited to, viral transduction, cationic liposomal transfection, multi-component lipid based transfection, calcium phosphate, DEAE-dextran, and direct delivery.

Multi-potent cells that contain the granulosa cell specific gene reporter can be selected for by any cell selection method known in the art. Examples of methods for cell selection include, but are not limited to, fluorescence activated cell sorting (FACS), differential adhesion, selection of precursor or progenitor cells for clonal expansion, and selection for antibiotic resistance.

Populations of multi-potent cells that contain the granulosa cell specific gene reporter are cultured under conditions suitable for differentiation of the mammalian multi-potent cells to granulosa cells or granulosa cell precursors. The multi-potent cells can be induced to differentiate by any methods commonly used in the art. By way of example, but not by limitations, undifferentiated ESCs containing granulosa cell specific gene reporter that are cultured on a mitotically-inactivated mouse embryonic fibroblast (MEF) feeder layer can be induced to differentiate by separating the ESCs from the MEF by differential adhesion and culturing the ESCs with 15% FBS in the absence of LIF on gelatin-coated plates in a monolayer. Other methods for differentiation include, but are not limited to, inducement by embryoid body formation in hanging droplets.

In some embodiments, growth factors or activators of signaling pathways for granulosa cell specification are used to direct multi-potent cell to differentiate into granulosa cells or granulosa cell precursors. Growth factors or activators of signaling pathways for granulosa cell specification, include, but are not limited to bFGF or activators of the Notch signaling pathway, e.g., Jagged1 or Jagged2.

After inducement of differentiation of the population of multi-potent cells, granulosa cells or granulosa cell precursors are identified and isolated. In some embodiments, the granulosa cells or granulosa cell precursors are identified by the expression of fluorescence under the control of the granulosa cell-specific gene. In some embodiments, the granulosa cells or granulosa cell precursors are isolated into enriched populations of granulosa cells or granulosa cell precursors by FACS, antibody-based immunomagnetic sorting (e.g., magnetic assisted cell sorting (MACS)), differential adhesion, clonal selection and expansion, or antibiotic resistance.

In some embodiments, the granulosa cells or granulosa cell precursors are isolated using a cell surface markers(s) selective for or specific to granulosa cells or granulosa cell precursors. Examples of cell surface markers selective for or specific to granulosa cells or granulosa cell precursors include, but are not limited to anti-mullarian hormone receptor, and Notch receptor (Notch2).

Methods for Growth and Maturation of Follicles and Immature Oocytes in Ovarian Tissue In some embodiments, enriched populations of granulosa cells or granulosa cell precursors are used to promote the growth and maturation of follicles, follicle-like structures, and/or immature oocytes in ovarian tissue.

In some embodiments, ovarian tissue is contacted by an enriched population of granulosa cells or granulosa cell precursors wherein the granulosa cells or granulosa cell precursors promote the growth and maturation of follicles, follicle-like structures, and/or immature oocytes in ovarian tissue. In some embodiments, after contact with the ovarian tissue, the granulosa cells or granulosa cell precursors migrate to follicles, follicle-like structures, and/or immature oocytes or oocyte precursors in ovarian tissue to produce or enrich an ovarian somatic environment that induces maturation of follicles and immature oocytes.

In some embodiments, the ovarian tissue is contacted by an enriched population of granulosa cells or granulosa cell precursors in vivo. In some embodiments, in vivo administration includes, but is not limited to, localized injection (e.g., catheter administration or direct intra-ovarian injection), systemic injection, intravenous injection, intrauterine injection, and parenteral administration.

In some embodiments, the ovarian tissue is contacted by an enriched population of granulosa cells or granulosa cell precursors ex vivo. In some embodiments, ex vivo contact includes, but is not limited to, direct injection of ovarian tissue, aggregation with intact or dissociated ovarian tissue, and co-culture with ovarian tissue. In some embodiments, the contacted ex vivo ovarian tissue is cultured and then transplanted or implanted into a subject's ovaries or surrounding tissues. Methods for transplanting or implanting include, but are not limited to, engraftment onto ovary, injection or engraftment of tissue into ovary following ovarian incision, and engraftment into fallopian tube.

In some embodiments, the contacted ex vivo ovarian tissue is cultured and then frozen and stored after growth and maturation of the follicle and/or oocyte.

The ovarian tissue may be any mammalian ovarian tissue. Mammals from which the ovarian tissue can originate, include, for example, farm animals, such as sheep, pigs, cows, and horses; pet animals, such as dogs and cats; laboratory animals, such as rats, mice, monkeys, and rabbits. In some embodiments, the mammal is a human.

In some embodiments, the enriched population of granulosa cells or granulosa cell precursors and the ovarian tissue are autologous. In some embodiments, the enriched population of granulosa cells or granulosa cell precursors and the ovarian tissue are heterologous allogeneic.

In some embodiments, the promotion of growth and maturation of follicles, follicle-like structures, and/or immature oocytes or oocyte precursors in ovarian tissue by granulosa cells or granulosa cell precursors is measured by an increase in follicle diameter, increase in granulosa cell number, increase in steroid hormone production, increase in oocyte diameter, or a combination thereof.

The diameter of a maturing follicle or oocyte varies from species to species and is identifiable by one skilled in the art since mature follicle sizes for specific species is generally known in the art. By way of example, but not by limitation, in some embodiments, a follicular diameter of a human follicle that is indicative of a mature or maturing follicle is a diameter greater than about 30 µm. Alternatively, or additionally, a follicular diameter of a human follicle that is indicative of a mature or maturing follicle is a diameter between about 30 µm to 10,000 µm, between about 50 µm to 5000 µm, between about 100 µm to 2000 µm, between about 200 µm to 1000 µm, between about 300 µm to 900 µm, between about 400 µm to 800 µm, or between about 500 µm to 700 µm.

By way of example, but not by limitation, in some embodiments, an oocyte diameter of a human oocyte that is indicative of a mature or maturing oocyte is a diameter greater than about 10 µm. Alternatively, or additionally, a follicular diameter of a human follicle that is indicative of a mature or maturing oocyte is a diameter between about 10 µm to 200 µm, or between about 20 µm to 175 µm, or between about 30 µm to 150 µm, or between about 40 µm to 125 µm, or between about 50 µm to 100 µm, or between about 60 µm to 75 µm.

In some embodiments, an increase in granulosa cell number in ovarian tissue is measured by comparison of the number of granulosa cells in the ovarian tissue before contact with granulosa cells or granulosa cell precursors to the number of granulosa cells in the ovarian tissue after contact with granulosa cells or granulosa cell precursors. Alternatively, or additionally, an increase in granulosa cell number in ovarian tissue is measured by comparison of the number of granulosa cells in the ovarian tissue after contact with granulosa cells or granulosa cell precursors as compared to age-matched ovarian tissue not contacted with granulosa cells or granulosa cell precursors.

In some embodiments, the increase in granulosa cell number in ovarian tissue contacted with granulosa cells or granulosa cell precursors is measured as a percent increase of about 1%, 5%, 10%, 20%, 30%, 40%, 50%, 60%, 70%, 80%, 90%, 100% or a percent increase between any two of these values as compared to, e.g., ovarian tissue before contact with granulosa cells or granulosa cell precursors or age-matched ovarian tissue not contacted with granulosa cells or granulosa cell precursors.

Steroid hormones produced by the contacting of granulosa cells or granulosa cell precursors with ovarian tissue include, but are not limited to, estradiol, estriol, estrone, pregnenolone, and progesterone. In some embodiments, the increase in steroid hormones produced in ovarian tissue contacted with granulosa cells or granulosa cell precursors is measured as a percent increase of about 1%, 5%, 10%, 20%, 30%, 40%, 50%, 60%, 70%, 80%, 90%, 100% or a percent increase between any two of these values as compared to, e.g., ovarian tissue before contact with granulosa cells or granulosa cell precursors or age-matched ovarian tissue not contacted with granulosa cells or granulosa cell precursors.

Methods for Increasing Steroidal Hormones in a Subject

In some embodiments, an effective amount of an enriched population of granulosa cells or granulosa cell precursors is administered to a subject to increase steroidal hormones.

In some embodiments, the granulosa cells or granulosa cell precursors secrete steroidal hormones. Alternatively, or additionally, in some embodiments, the granulosa cells or granulosa cell precursors are stimulated to secrete steroidal hormones by stimulating agents.

Steroidal hormones secreted by the granulosa cells or granulosa cell precursors include, but are not limited to, estradiol, estriol, estrone, pregnenolone, and progesterone.

Stimulating agents include, but are not limited to, follicle-stimulating hormone (FSH), 8-Bromoadenosine 3',5'-cyclic monophosphate (8-br-cAMP), and luteinizing hormone (LH).

In some embodiments, the granulosa cells or granulosa cell precursors are stimulated before administration to the subject, i.e., the granulosa cells or granulosa cell precursors are stimulated ex vivo to secrete steroidal hormones. In some embodiments, the granulosa cells or granulosa cell precursors are stimulated after administration to the subject, i.e., the granulosa cells or granulosa cell precursors are stimulated in vivo to secrete steroidal hormones.

In some embodiments, the enriched population of granulosa cells or granulosa cell precursors is autologous to the subject. In some embodiments, the enriched population of granulosa cells or granulosa cell precursors is heterologous to the subject.

In some embodiments, the subject suffers from reduced or lack of secretion of steroidal hormones. In some embodiments, the reduced or lack of secretion of steroidal hormones is due to menopause, ovariectomy, hysterectomy, premature ovarian failure, primary ovarian insufficiency, chemotherapy-induced ovarian failure, Turner's syndrome.

In some embodiments, an increase in steroidal hormones in a subject in need thereof is based on a comparison between steroidal hormone levels in the subject before administration of the granulosa cells or granulosa cell precursors to steroidal hormone levels in the subject after administration of the granulosa cells or granulosa cell precursors.

In some embodiments, an increase in steroidal hormones in a subject is based on the steroidal hormone levels in a subject after administration of granulosa cells or granulosa cell precursors as compared to steroidal hormone levels in a subject, who is sex and aged matched to the treated subject and not administered granulosa cells or granulosa cell precursors.

In some embodiments, the increase in steroidal hormones produced in a subject administered granulosa cells or granulosa cell precursors is measured as a percent increase of about 1%, 5%, 10%, 20%, 30%, 40%, 50%, 60%, 70%, 80%, 90%, 100% or a percent increase between any two of these values as compared to, e.g., the subject before contacting with granulosa cells or granulosa cell precursors or a sex and aged matched subject not administered granulosa cells or granulosa cell precursors.

The effective amount of granulosa cells or granulosa cell precursors may be determined during pre-clinical trials and clinical trials by methods familiar to physicians and clinicians. An effective amount of granulosa cells or granulosa cell precursors useful in the methods may be administered to a subject in need thereof by any of a number of well-known methods for administering cells. The dose and/or dosage regimen will depend upon the characteristics of the condition being treated, e.g., the subject is in menopause or the subject had a hysterectomy, the subject, and the subject's history.

Any method known to those in the art for administration of cells as a therapy may be employed. In some embodiments, the granulosa cells or granulosa cell precursors are administered to the subject, e.g., localized injection (e.g., catheter administration or direct intra-ovarian injection), systemic injection, intravenous injection, intrauterine injection, and parenteral administration. By way of example, but not by limitation, in some embodiments, granulosa cells or granulosa cell precursors are directly injected into ovarian tissue or ovaries.

In some embodiments, the subject is a mammal Mammalian subjects, include, but are not limited to, farm animals, such as sheep, pigs, cows, and horses; pet animals, such as dogs and cats; laboratory animals, such as rats, mice, monkeys, and rabbits. In some embodiments, the mammal is a human.

Kits

In some embodiments, the present technology relates to kits for producing an enriched population of granulosa cells or granulosa cell precursors. In some embodiments, the kit includes at least one granulosa cell specific reporter.

In some embodiments, the granulosa cell specific reporter includes a fluorescent reporter under regulatory control of an ovarian granulosa cell-specific gene. Fluorescent reporters include but are not limited to, *Discosoma* sp. red (DsRed), green fluorescent protein (GFP), yellow fluorescent protein (YFP), and orange fluorescent protein (OFP).

In some embodiments, the granulosa cell specific reporter is a non-fluorescent reporter under regulatory control of an ovarian granulosa cell-specific gene. Non-fluorescent reporters include, but are not limited to, luciferase and beta-galactosidase.

Ovarian granulosa cell-specific genes include, but are not limited to, forkhead box L2 (Foxl2), wingless type MMTV integration site family, member 4 (WNT4), Nr5a1, Dax-1, ATP-binding cassette, subfamily 9 (Abca9), acetyl-Coenzyme A acyltransferase 2 (mitochondrial 3-oxoacyl-Coenzyme A thiolase; Acaa2), actin, alpha 2, smooth muscle, aorta (Acta2), a disintegrin-like and metallopeptidase (reprolysin-like) with thrombosin type 1 motif, 17 (Adamts17), ADAMTS-like 2 (Adamts12), AF4/FMR2 family, member 1 (Aff1), expressed sequence AI314831 (AI314831), Aldo-keto reductase family 1, member C14 (Akr1c14), aldo-keto reductase family 1, Notch2, and member C-like (Akr1c1).

In some embodiments, the granulosa cell specific reporter is in a delivery vector. Delivery vectors include, but are not limited to, a plasmid and viral vector.

In some embodiments, the kit also includes a plurality of multi-potent cells. Multi-potent cells include, but are not limited to, embryonic stem cells (ESCs), pluripotent stem cells, induced pluripotent stem cells (iPSCs) or otherwise reprogrammed somatic cells, bone marrow derived cells, peripheral blood-derived cells.

The multi-potent cells may be any mammalian multi-potent cell. Mammals from which the multi-potent cell can originate, include, for example, farm animals, such as sheep, pigs, cows, and horses; pet animals, such as dogs and cats; laboratory animals, such as rats, mice, monkeys, and rabbits. In some embodiments, the mammal is a human.

In some embodiments, the kit also includes reagents for inserting the granulosa cell specific reporter into the multi-potent cells. In some embodiments, the kit also includes reagents for culturing the multi-potent cells.

In some embodiments, the kit also includes instructions for how to use the kit components to produce an enriched population of granulosa cells or granulosa cell precursors. By way of example, but not by limitation, in some embodiments, the instruction would disclose how to insert the granulosa specific reporter into multi-potent cells, how to induce differentiation of the multi-potent cells, and how to isolate granulosa cells or granulosa cell precursors.

EXAMPLES

The present examples are non-limiting implementations of the use of the present technology.

Example 1. Follicle-Like Structure Formation in Differentiating ESC Cultures

This example shows that differentiation of ESCs leads to the formation of follicle-like structures.

Materials and Methods

An undifferentiated mouse XX ESC line with germ cell lineage expression of green fluorescent protein (GFP) was generated from TgOG2 (ΔPE-Pou5f1-Gfp) transgenic female mice using standard methods, essentially as described in Hubner et al., *Science*, 300: 1251-56 (2003).

Undifferentiated TgOG2 ESCs were maintained on a mitotically-inactivated mouse embryonic fibroblast (MEF) feeder layer in DMEM supplemented with 15% heat-inactivated ESC-grade fetal bovine serum (FBS; Invitrogen, Carlsbad, Calif.), 1% sodium pyruvate, 1% non-essential amino acids, 1% penicillin-streptomycin (Invitrogen), 103 U/ml leukemia inhibitory factor (LIF; Millipore, Billerica, Mass.) and 0.1 mM β-mercaptoethanol (Sigma-Aldrich, St.

Louis, Mo.). For differentiation, ESCs were separated from MEFs by differential adhesion, and cultured with 15% FBS in the absence of LIF on gelatin-coated plates in a monolayer, as described in Hubner et al., Science, 300: 1251-56 (2003).

Live cell imaging was performed using a Nikon Eclipse TE2000-S inverted fluorescent microscope and SPOT imaging software (Diagnostic Instruments, Sterling Heights, Mich.).

Results

Expression of GFP was detected in undifferentiated TgOG2 ESC colonies (FIG. 1A), whereas the initiation of differentiation by removal of MEFs and LIF resulted in a progressive loss of widespread GFP expression over the next 3-7 days (FIG. 1B). Formation of distinct colonies comprised of GFP-positive cells occurred between days 7-26 after the initiation of differentiation (FIG. 1C-1D). Follicle-like structures consisting of a single large GFP-positive oocyte-like cell surrounded by somatic cells were detected between days 16-40 of differentiation (FIG. 1E).

The results show that ESCs can spontaneously differentiate into follicle-like structures.

Example 2. Granulosa Cell Specification and Isolation

This example shows a method for tracking and identifying granulosa cells that differentiate from ESCs.

Materials and Methods

Figure 2:
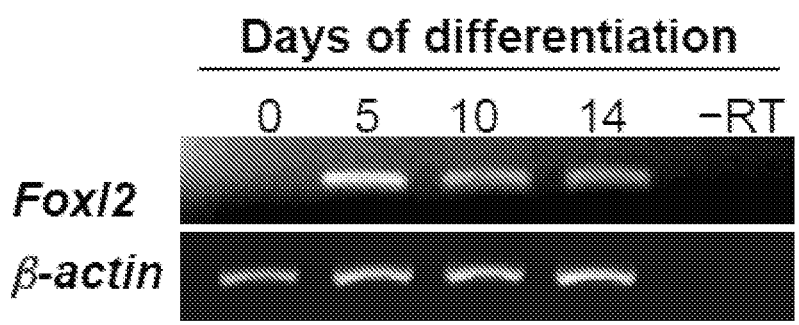
FIG. 2A is an image showing Foxl2 expression in differentiating ESCs but not in undifferentiated cells (day 0). β-actin, positive PCR control gene for sample loading; –RT, RNA sample lacking reverse transcriptase.
FIG. 2B is a diagram showing the conserved elements of the human (H) Foxl2 and mouse (M) Foxl2 gene promoters.
FIG. 2C is an image showing that DsRed is expressed in mouse granulosa cells, but not in 293 cells, following transfection with the Foxl2-DsRed construct.
FIG. 2D is an image showing that at day 1 of initiation of differentiation of TgOG2 ESCs co-expressing Foxl2-DsRed there is GFP expression and no DsRed expression.
FIG. 2E is an image showing that initiation of differentiation of TgOG2 ESCs co-expressing Foxl2-DsRed results in the gradual loss of GFP expression (days 1 to 5), with minimal GFP detected 5 days after initiation of differentiation, but there is observation of DsRed 5 days following initiation of differentiation.
FIG. 2F-2G are images showing that 9 days post initiation of differentiation the GFP signal returns and Foxl2-DsRed-expressing cells are nearly exclusively co-localized with GFP-expressing cell clusters.
Figure 2:
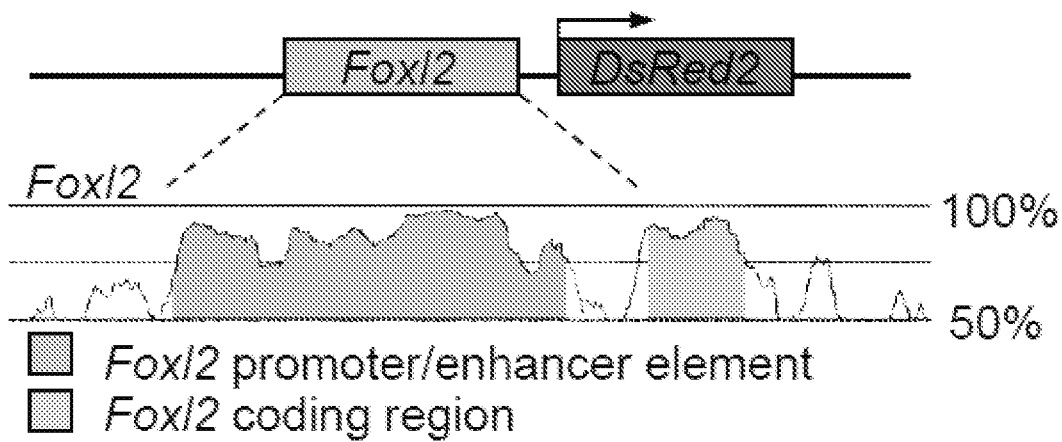
Figure 2:
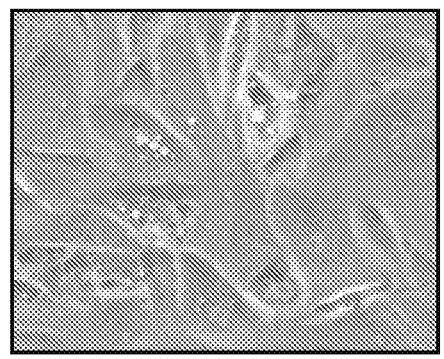
Figure 2:
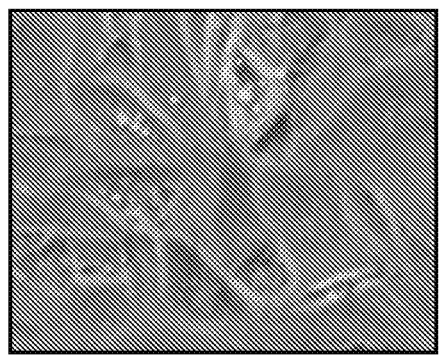
Figure 2:
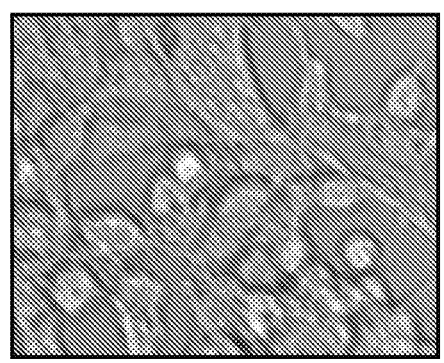
Figure 2:
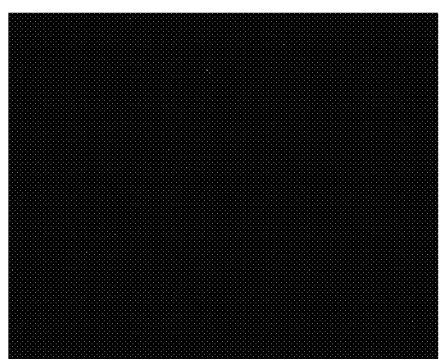
Figure 2:
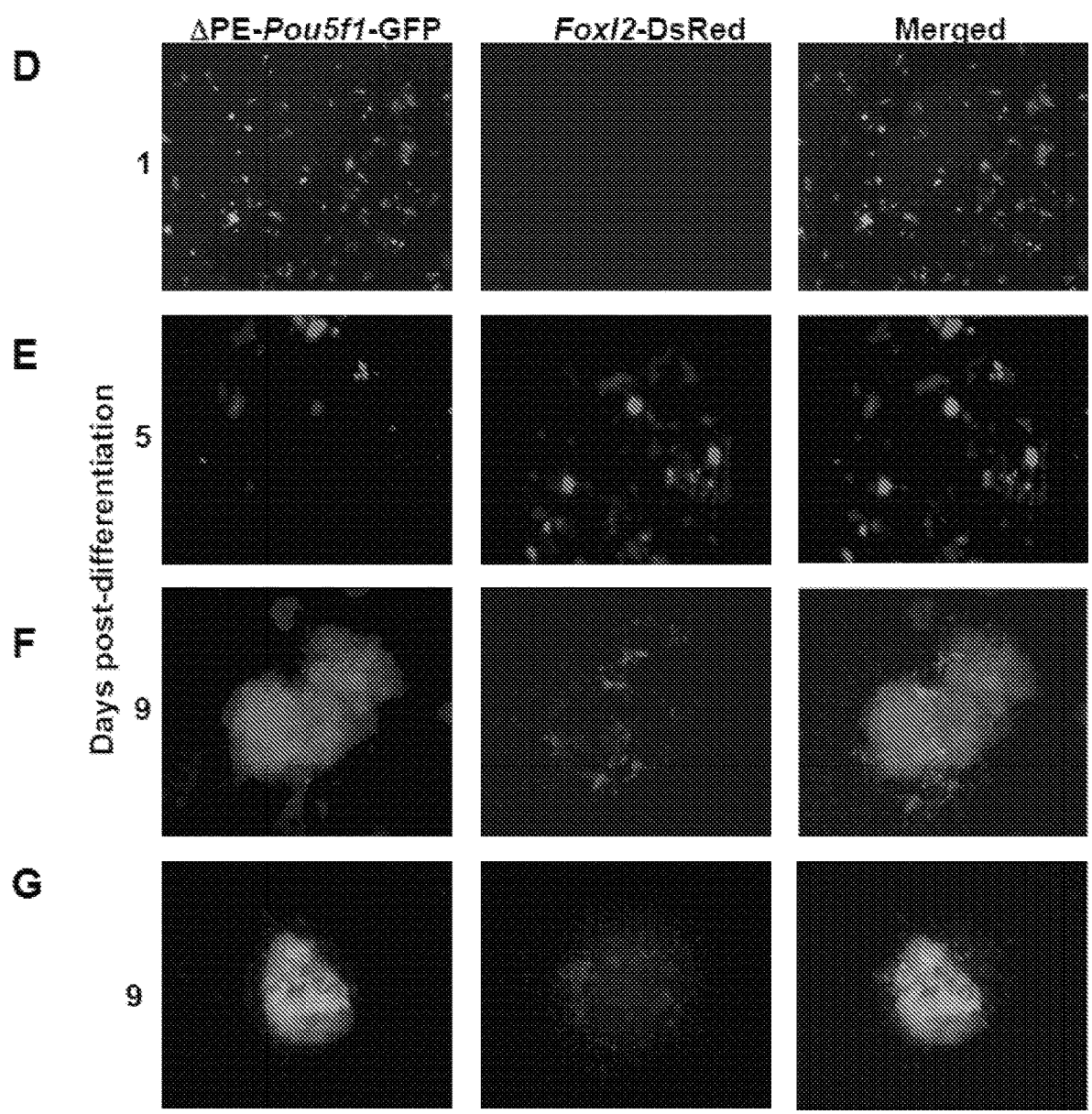

To identify and track ovarian somatic cells in differentiating ESC cultures, the expression of the early granulosa cell marker, Foxl2, in differentiating ESC cultures was mapped. The mapping revealed activation of the Foxl2 gene by day 5 (FIG. 2A). A 739 bp region of the Foxl2 gene promoter was identified using Genome Vista. The region was isolated from mouse genomic DNA and cloned into the pDsRed2-1 vector (Clontech, Mountain View, Calif.,) or the pLenti6 lentiviral construct containing the complete open reading frame of DsRed (Gateway Lentiviral System; Invitrogen), thus creating a DsRed expression vector under control of the Foxl2 gene promoter (FIG. 2B)

Promoter activity and specificity were verified using mouse granulosa cells as a positive control and 293 cells (Invitrogen) as a negative control (FIG. 2C). To verify the Foxl2 gene promoter-driven DsRed expression, undifferentiated TgOG2 ESCs were stably transfected with the Foxl2-pDsRed2-1 construct via electroporation, followed by clonal selection and expansion. Alternatively, ESCs were virally transduced following initiation of differentiation using viral supernatant produced by 293 cells transfected with the Foxl2-DsRed lentiviral construct (pLenti6-Foxl2-DsRed). Cells were analyzed for expression of DsRed by fluorescence microscopy and isolated by fluorescence-activated cell sorting (FACS).

For FACS, differentiating ESCs were removed from the plate by either 0.25% trypsin-EDTA (prior to day 10 of differentiation) or manually scraped. The cells were then incubated with 800 U/ml of type IV collagenase (Worthington, Lakewood, N.J.) with gentle dispersion for 15 minutes followed by incubation with 0.25% trypsin-EDTA for 10 minutes to obtain single cell suspensions (after day 10 of differentiation). Cells were prepared for FACS by resuspension in 1×-concentrated phosphate-buffered saline (PBS) containing 0.1% FBS and filtration (35-µm pore size). The cells were analyzed and sorted using a FACS Aria flow cytometer (BD Biosciences, San Jose, Calif.).

Estradiol and progesterone concentrations were measured in culture medium from FACS-purified Foxl2-DsRed-positive cells that had been re-plated and cultured for 24, 48 or 72 hours in the presence of PBS (vehicle), 100 ng/ml follicle stimulating hormone (FSH; NIDDK, NIH, Bethesda, Md.) or 1 mM 8-bromoadenosine-3',5'-cyclic monophosphate (8-br-cAMP; Sigma-Aldrich). Androgen substrate necessary for aromatization to estrogen was provided by the presence of heat-inactivated 15% FBS in all cultures, which contained 0.92 µg/ml androgen (mean of 56 lots of FBS tested). The estradiol ELISA was from Alpco (Salem, N.H.), and the progesterone ELISA was from DRG International (Mountainside, N.J.). All assays were performed according to the manufacturer's guidelines.

Results

Undifferentiated TgOG2 ESCs with stably transfected Foxl2-DsRed vector where induced to differentiate by removing MEFs and LIF. Cells positive for DsRed expression were absent on day 1 (FIG. 2D), but were observed as early as day 5 of differentiation (FIG. 2E). By day 9, DsRed expressing cells were found in close association with GFP-expressing colonies (FIG. 2F-2G). Notably, DsRed-expressing cells were nearly exclusively co-localized with GFP-expressing cell clusters at this time (FIG. 2F-2G).

Figure 3:
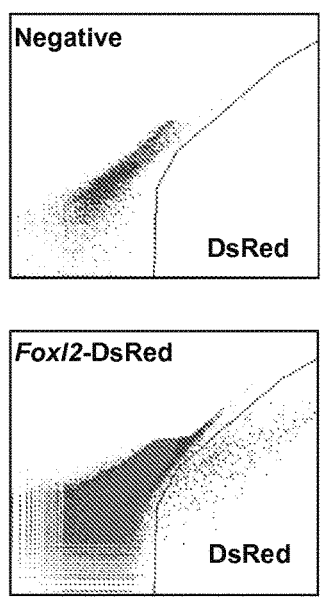
FIG. 3A are images showing that DsRed-expressing cells are detectable by day 5 of differentiation and can be isolated by FACS (Negative, parallel sorts of TgOG2 ECSs lacking Foxl2-DsRed).
FIG. 3B is an image showing expression of early granulosa cell markers in Foxl2-DsRed-expressing cells isolated by FACS at the indicated days of differentiation (–RT, RNA sample lacking reverse transcriptase; β-actin, positive PCR control gene for sample loading).
Figure 3:
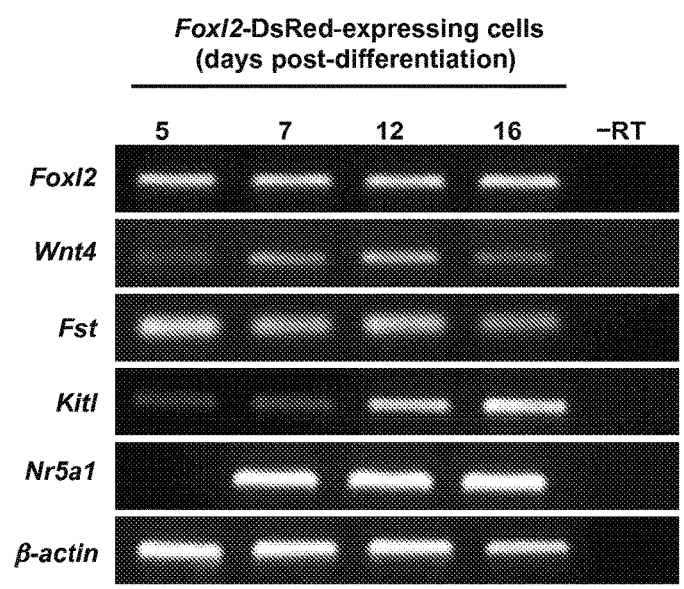

Gene expression analysis of DsRed-positive cells isolated by FACS at day 5 of differentiation (FIG. 3A) revealed a distinct somatic cell gene expression profile consistent with the presence of early stage ovarian granulosa cells (FIG. 3B). The mRNAs detected were Foxl2, Wingless-related MMTV integration site 4 (Wnt4), follistatin (Fst) and Kit ligand (Kitl; also referred to as stem cell factor or Scf, or Steel factor). Expression of nuclear receptor subfamily 5 group A member 1 (Nr5a1; also referred to as steroidogenic factor-1 or Sf-1) became detectable by day 7 (FIG. 3B).

Figure 4:
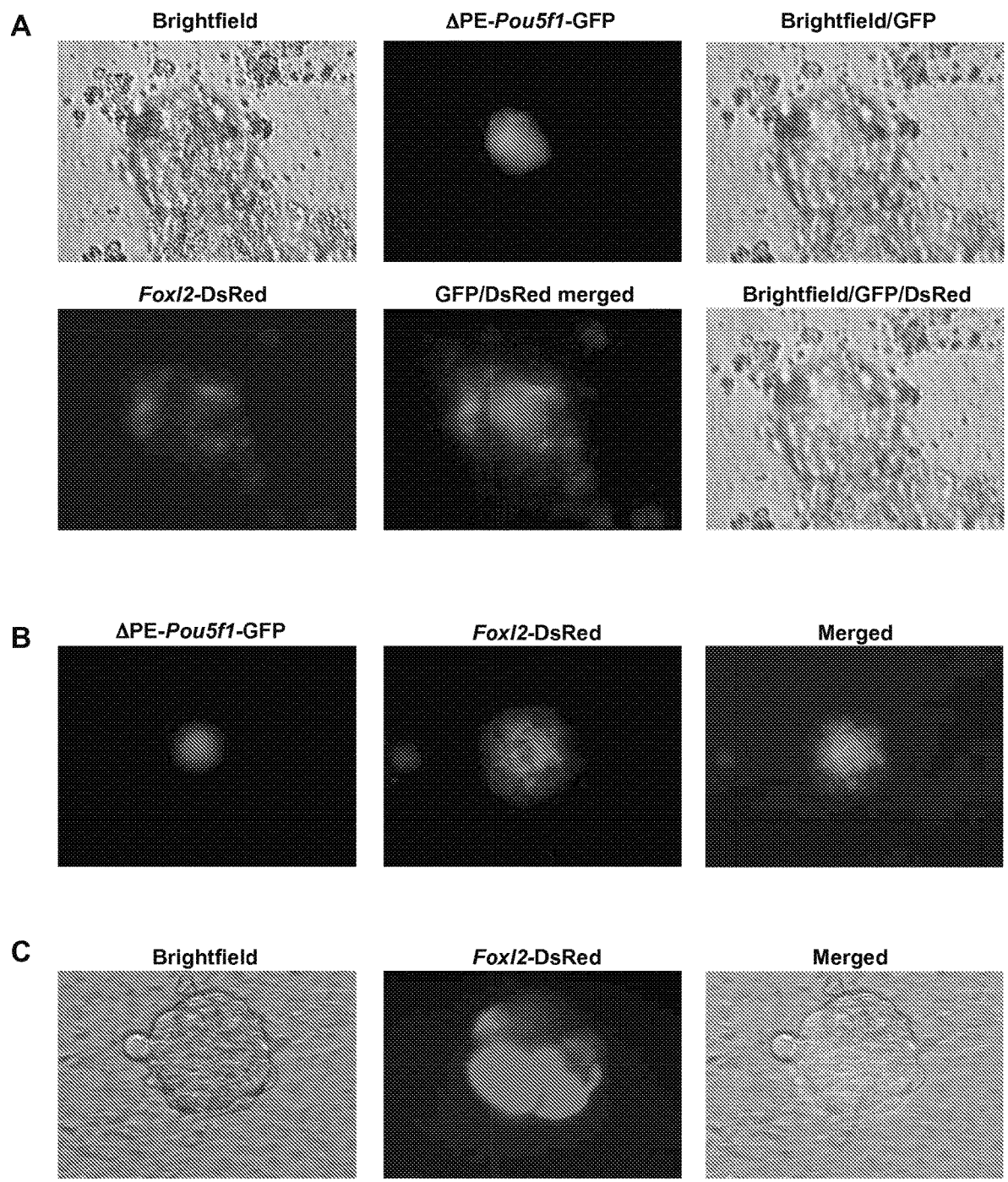
FIG. 4A is an image showing follicle-like structures formed in cultures of TgOG2 ESCs co-expressing Foxl2-DsRed at 16 days. ΔPE-Pou5f1-driven GFP expression is detectable in a single large cell surrounded by multiple Foxl2-DsRed-expressing cells.
FIG. 4B is an image showing follicle-like structures formed in cultures of TgOG2 ESCs co-expressing Foxl2-DsRed at 40 days. ΔPE-Pou5f1-driven GFP expression is detectable in a single large cell surrounded by multiple Foxl2-DsRed-expressing cells.
FIG. 4C is an image showing DsRed-expressing cells are detectable in follicle-like structures formed by v6.5 ESCs, transduced with Foxl2-DsRed, following 16 days of differentiation.

On day 16 of differentiation, and continuing through day 40, multi-dimensional follicle-like structures, each one consisting of a single large (25-50 µm) GFP-positive cell surrounded by DsRed-expressing cells, were observed by direct fluorescence (FIG. 4A-4B). To ensure that these observations were not specific to the TgOG2 ESC line, v6.5 ESCs that were transduced with Foxl2-DsRed also formed the same follicle-like structures comprised of a centrally located oocyte-like cell surrounded by DsRed-expressing somatic cells following the induction of differentiation for at least 16 days (FIG. 4C).

Figure 5:
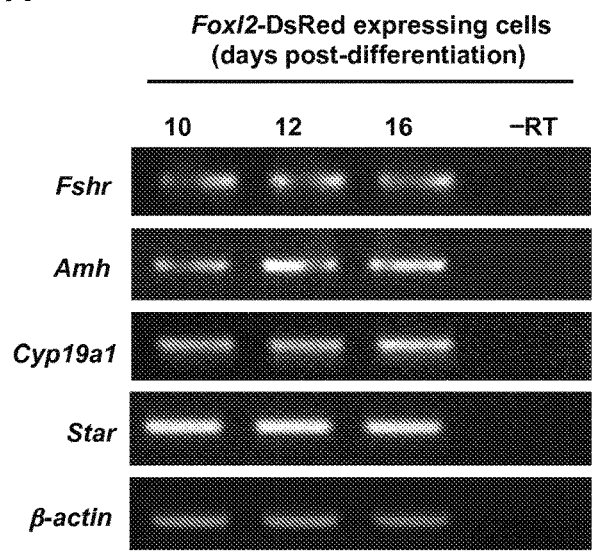
FIG. 5A is an image showing Foxl2-DsRed positive cells isolated from ESC cultures between days 10-16 after initiation of differentiation express markers of differentiating granulosa cells (–RT, RNA sample lacking reverse transcriptase; β-actin, positive PCR control gene for sample loading).
FIG. 5B is a graph showing estradiol production by FACS-purified Foxl2-DsRed positive cells ($2 \times 10^3$ cells per well) maintained in culture for up to 3 days (FSH, 100 ng/ml; 8-br-cAMP, 1 mM). Data are the mean±SEM of 3 independent cultures (*, $P<0.05$ versus vehicle control).
FIG. 5C is a graph showing progesterone production by FACS-purified Foxl2-DsRed positive cells ($2 \times 10^3$ cells per well) maintained in culture for up to 3 days (FSH, 100 ng/ml; 8-br-cAMP, 1 mM). Data are the mean±SEM of 3 independent cultures (*, $P<0.05$ versus vehicle control).
Figure 5:
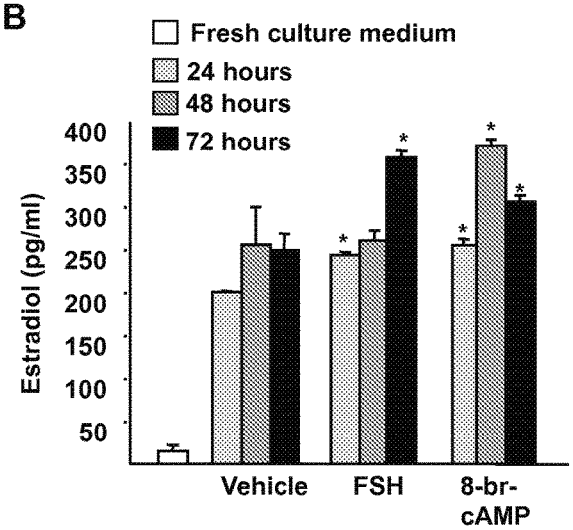
Figure 5:
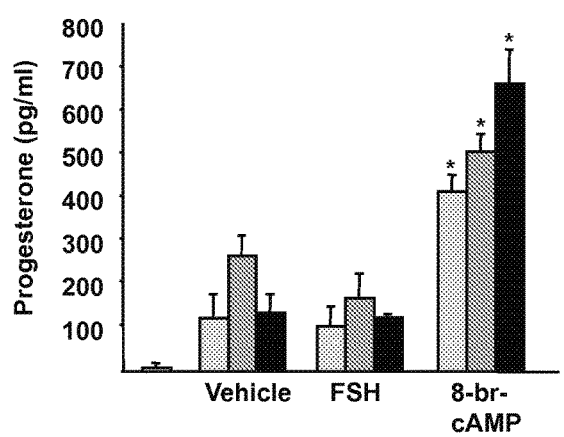

Gene expression analysis of DsRed-expressing cells isolated by FACS on day 10 of differentiation revealed the presence of multiple markers classically associated with differentiating granulosa cells, including follicle-stimulating hormone receptor (Fshr), anti-Müllerian hormone (Amh; also referred to as Müllerian-inhibiting substance or Mis), cytochrome P450 family 19 subfamily a polypeptide 1 (Cyp19a1; also referred to as aromatase) and steroidogenic acute regulatory protein (StAR) (FIG. 5A). Evaluation of steroidogenesis following subculture of DsRed-positive cells isolated on day 12 of differentiation revealed the presence of both estradiol and progesterone in the culture medium (FIG. 5B-5C). Additionally, the treatment with either FSH or 8-br-cAMP led to a significant increase in estradiol production, which confirmed the presence of functional FSH receptors and cAMP-mediated signaling coupled to steroidogenesis in these cells. However, only 8-br-cAMP was able to significantly enhance progesterone production (FIG. 5C).

These results show that multi-potent cells can differentiate into granulosa cells or granulosa cell precursors. Additionally, the results show that the granulosa cells or granulosa cell precursors derived from the multi-potent cells can be tracked and identified by a granulosa cell specific gene reporter, which can also be used to isolate granulosa cells or granulosa cell precursors, e.g., by FACS. Accordingly, multi-potent cells containing granulosa cell specific gene reporters are useful for tracking and isolating populations of granulosa cells or granulosa cell precursors.

Example 3. Intraovarian Transplantation of Granulosa Cells

This example shows granulosa cells derived from multi-potent cells migrate to immature oocytes and developing follicles in neo-natal ovaries.

Materials and Methods

Wild-type C57BL/6 female mice (Charles River Laboratories, Wilmington, Mass., USA) were used in the following experiments.

Figure 6:
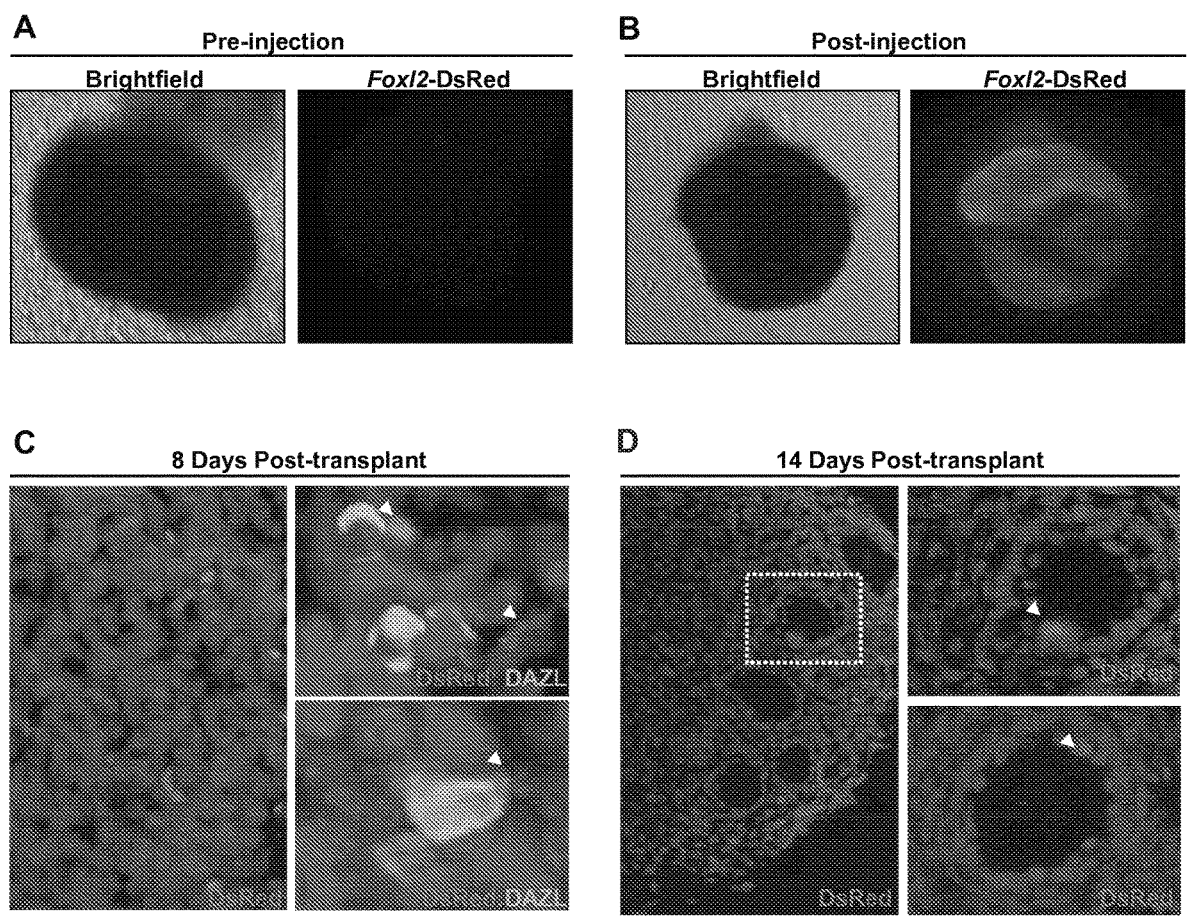
FIG. 6A is an image showing wild-type neonatal ovary before injection of Foxl2-DsRed-expressing cells isolated from ESC cultures 12 days post-differentiation.
FIG. 6B is an image showing wild-type neonatal ovary after injection of Foxl2-DsRed-expressing cells isolated from ESC cultures 12 days post-differentiation.
FIG. 6C is an image showing DsRed-expressing cells are present within the ovarian stroma at 8 days post-transplant (left); by dual immunofluorescence, these cells frequently associate with immature oocytes, identified by expression of the oocyte marker Dazl (green; right panels).
FIG. 6D is an image showing that DsRed-expressing cells are found only in the granulosa cell layer of growing follicles at 14 days post-transplant.

Following differentiation of Foxl2-DsRed-expressing ESCs for 12 days, FACS was used to isolate DsRed-positive cells. For each experiment, 200-500 DsRed-positive cells were microinjected into a single neonatal (day 2-4 postpartum) wild-type mouse ovary using a Pneumatic PicoPump (World Precision Instruments, Sarasota, Fla.) (FIG. 6A-6B). Injected ovaries were then transplanted under kidney capsules of ovariectomized wild-type female mice at 6 weeks of age. At 8 days and 2 weeks post-transplantation, the grafted ovaries were removed and fixed in 4% paraformaldehyde (PFA) for analysis.

Fixed ovaries were embedded in paraffin, serially sectioned, mounted on slides and de-waxed in xylenes, followed by hydration in a graded ethanol series. Antigen retrieval was performed by boiling the slides for 5 min in sodium citrate (pH 6.0), followed by blocking in TNK buffer (0.1 M Tris, 0.55 M NaCl, 0.1 mM KCl, 1% goat serum, 0.5% bovine serum albumin and 0.1% Triton-X in PBS), incubation with the desired primary antibody (1:100 dilution) overnight at 4° C., and fluor-conjugated secondary antibody (1:250 dilution, Alexa Fluor-488 or -568; Invitrogen) at 20° C. for 1 hour. Primary antibodies used were mouse anti-Dazl antibody from Serotec (MCA2336; Raleigh, N.C.) and rabbit anti-RFP antibody for detection of DsRed from Abcam (ab62341; Cambridge, Mass.). Fluorescence image analysis was performed using a Nikon Eclipse TE2000-S inverted fluorescent microscope and SPOT imaging software (Diagnostic Instruments).

Results

Wild-type neonatal ovary before injection of Foxl2-DsRed-expressing cells isolated from ESC cultures 12 days post-differentiation show no DsRed (FIG. 6A). After injection of Foxl2-DsRed-expressing cells isolated from ESC cultures 12 days post-differentiation, wild-type neonatal ovary displayed DsRed (FIG. 6B).

At 8 days post-transplantation, DsRed-expressing cells were found distributed throughout the stroma of the injected ovaries. Many of these cells were observed in close proximity to immature oocytes, as indicated by dual-immunofluorescence staining for DsRed and the oocyte marker Dazl (Deleted in azoospermia-like) (FIG. 6C). At 14 days post-transplantation, DsRed-expressing cells were no longer observed in the stroma but were detected exclusively within the granulosa layer of growing follicles (FIG. 6D).

These results show that granulosa cells and granulosa cell precursors naturally migrate to developing follicles or immature oocytes. Accordingly, granulosa cells and granulosa cell are useful for promoting the growth and maturation of follicles, follicle-like structures, and immature oocytes.

Example 4. Method for Promoting Growth and Maturation of a Follicle or Follicle-Like Structure This example will show that granulosa cells promote the growth and maturation of follicles and immature oocytes.

Materials and Methods

Aged and sex matched, human subjects are divided into two groups. One group is administered granulosa cells by direct injection into the ovaries, wherein the granulosa cells are engineered as described above from multi-potent cells from each individual, so that the granulosa cells are autologous to each individual. The second group (control) is not administered granulosa cells.

Using methods known in the art, the ovary tissue samples from each subject are removed and analyzed by methods known in the art to measure follicle diameter and oocyte diameter.

Results

It is anticipated that ovaries from subject treated with autologous granulosa cells will have follicles with diameters greater than 30 μm and/or oocytes greater than 10 μm.

These results will indicate that granulosa cells and/or granulosa cell precursors are useful for promoting the growth and maturation of follicles and immature oocytes.

Example 5. Method of Increasing Steroidal Hormones

This example will show that administration of granulosa cells to a subject in need thereof will increase levels of steroidal hormones in the subject.

Materials and Methods

Aged and sex matched, human subjects suffering from chemotherapy-induced ovarian failure are divided into two groups. One group is administered granulosa cells by direct injection into the ovaries, wherein the granulosa cells are engineered as described above from multi-potent cells from each individual, so that the granulosa cells are autologous to each individual. The second group (control) is not administered granulosa cells.

Using methods known in the art, levels of estradiol and progesterone will be measured in each subject.

Results

It is anticipated that subject administered autologous granulosa cells will have elevated levels of estradiol and progesterone as compared to the untreated subjects.

These results will indicate that granulosa cells and/or granulosa cell precursors are useful for increasing the levels of steroidal hormones in a subject in need thereof.

EQUIVALENTS

The present technology is not to be limited in terms of the particular embodiments described in this application, which are intended as single illustrations of individual aspects of the present technology. Many modifications and variations of the present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

What is claimed is:

1. A method to promote the growth and maturation of a follicle or an immature oocyte in a subject, the method comprising:
    introducing into a plurality of mammalian multi-potent cells a recombinant DNA construct comprising a reporter coding sequence under the control of a promoter of an ovarian granulosa cell-specific gene, wherein the ovarian granulosa cell-specific gene is forkhead box L2 (Foxl2), and said multi-potent cells comprising an expressed reporter have differentiated into granulosa cells or granulosa cell precursors;
    culturing the plurality of mammalian multi-potent cells comprising the recombinant DNA construct in vitro, under conditions suitable for differentiation of the multi-potent cells into the granulosa cells or the granulosa cell precursors;
    isolating an enriched population of the granulosa cells or the granulosa cell precursors, wherein the enrichment is based on expression of the reporter; and
    contacting the enriched population of cells comprising the granulosa cells or the granulosa cell precursors with mammalian ovarian tissue in vivo, wherein the mammalian ovarian tissue comprises at least one of the follicle and the immature oocyte, and wherein the granulosa cells or the granulosa cell precursors promote the growth and maturation of at least one of the follicle and the immature oocyte.

2. The method of claim 1, wherein the population comprising the granulosa cells or the granulosa cell precursors and the mammalian ovarian tissue are autologous.

3. The method of claim 1, wherein the mammalian ovarian tissue is human.

4. The method of claim 1, wherein the reporter is a fluorescent reporter.

5. The method of claim 4, wherein the fluorescent reporter is selected from the group consisting of: *Discosoma* sp. red (DsRed), green fluorescent protein (GFP), yellow fluorescent protein (YFP), and orange fluorescent protein (OFP).

6. The method of claim 1, wherein the mammalian multi-potent cells are selected from the group consisting of: embryonic stem cells (ESCs), induce pluripotent stem cells (iPSCs), reprogrammed somatic cells, bone marrow derived cells, and peripheral blood-derived cells.

* * * * *